United States Patent [19]

Foster et al.

[11] 4,448,644

[45] May 15, 1984

[54] METHOD OF PRODUCING ETHANOL-WATER AZEOTROPE FROM CRUDE ETHANOL

[75] Inventors: Brian R. Foster; William T. Woodfin, both of Hull, England

[73] Assignee: BP Chemicals Limited, London, England

[21] Appl. No.: 493,653

[22] Filed: May 12, 1983

Related U.S. Application Data

[63] Continuation of Ser. No. 326,362, Dec. 1, 1981, abandoned.

[30] Foreign Application Priority Data

Dec. 6, 1980 [GB] United Kingdom ................ 8039196

[51] Int. Cl.³ .......................... B01D 3/40; C07C 29/88
[52] U.S. Cl. ........................................ 203/37; 203/75; 203/76; 203/77; 203/DIG. 13; 203/DIG 19; 568/921
[58] Field of Search ................. 203/19, 37, 36, 75–85, 203/92–97, 99, DIG. 19, DIG. 13; 426/494; 435/161; 568/916, 921, 913

[56] References Cited

U.S. PATENT DOCUMENTS

| | | | |
|---|---|---|---|
| 2,801,209 | 7/1957 | Muller et al. | 203/83 |
| 3,265,594 | 8/1966 | DeJean et al. | 203/85 |
| 3,406,100 | 10/1968 | Karafian | 203/85 |
| 3,445,345 | 5/1969 | Katzen et al. | 203/85 |
| 4,308,109 | 12/1981 | Griffiths et al. | 203/DIG. 19 |

FOREIGN PATENT DOCUMENTS

10927 5/1980 European Pat. Off. .

Primary Examiner—Wilbur L. Bascomb, Jr.
Attorney, Agent, or Firm—Brooks, Haidt, Haffner & Delahunty

[57] ABSTRACT

This invention relates to a process for purifying crude ethanol, whether produced by fermentation or by the synthetic route, to produce a pure ethanol-water azeotrope. The process uses only two distillation columns for fermentation ethanol or synthetic ethanol eventhough the latter has diethyl ether as impurity. The inventive concept lies in the design and specification of the columns and the specific high pressure and low reflux ratio distillation conditions which enable each of the impurities in ethanol to be reduced below ppm. Ethanol of such purity is most desirable when used for potable or pharmaceutical purposes.

10 Claims, 1 Drawing Figure

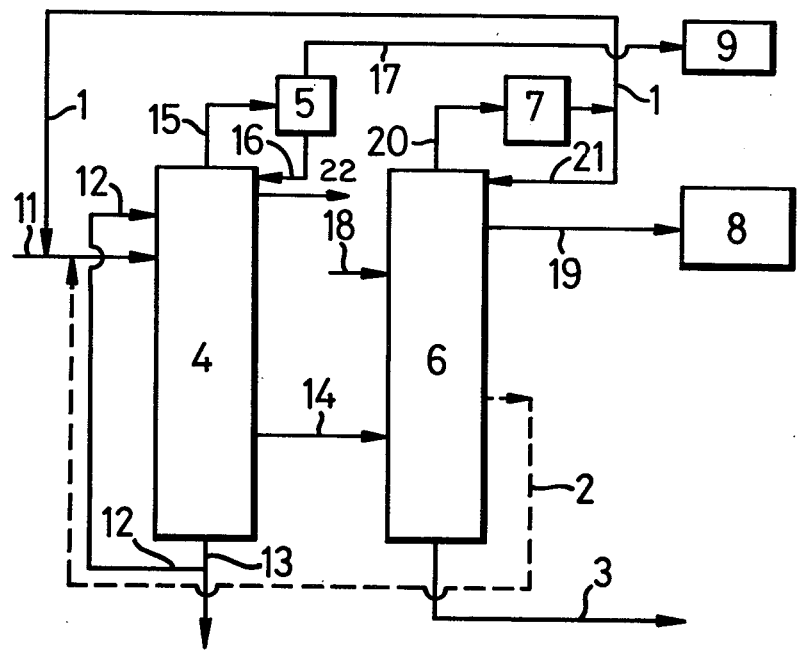

METHOD OF PRODUCING ETHANOL-WATER AZEOTROPE FROM CRUDE ETHANOL

This application is a continuation of application Ser. No. 326,362, filed Dec. 1, 1981, abandoned.

The present invention relates to a process for purifying crude ethanol to produce a substantially pure ethanol-water azeotrope which may be dried subsequently.

In conventional processes, the crude ethanol whether produced by fermentation or by the synthetic route e.g. by the hydration of ethylene, is in the form of a dilute aqueous solution and has always been subjected to a series of distillation and absorption stripping operations, to obtain an ethanol-water azeotrope essentially free from all impurities. These operations were designed to remove impurities such as, for instance, acetaldehyde, diethyl ether, and butanols. Depending upon the process by which the crude ethanol is made at least four columns and usually six or more columns have been used to obtain an ethanol-water azeotrope from which substantially all impurities have been removed.

To obtain this high purity product, the crude ethanol stream is normally first subjected to hydroselective distillation in one or more towers. The term hydroselective distillation is used to refer to a hydroextractive process in which the impurities and the desired product components are separated in such a manner that neither the impurities nor the desired product components leave the column with the extractant. Very considerable dilution of the crude ethanol by water produces an inversion of volatilities, so that the impurities such as higher alcohols, e.g. butanols, can be removed overhead in the hydroselective distillation. The relatively lower boiling impurities, such as acetaldehyde and ether normally remain more volatile and are also removed overhead. Aqueous ethanol stripped of impurities is removed as a sidestream fraction from the lower part of the hydroselective distillation column, and is then concentrated or rectified, typically in the presence of alkali, in the next column normally known as the rectifier, to produce ethanol-water azeotrope as a sidestream fraction from the upper part of the column free of higher boiling impurities such as butanols. As a rule a small lower sidestream of butanols, which have escaped removal in the hydroselective distillation, is also removed from the rectifier and is further processed in an additional column termed the butanol column to recover ethanol for recycle. The base product from the rectifier consists of relatively pure but dilute aqueous ethanol and this is normally fed to a stripper column, which recovers the ethanol as an overhead fraction for recycle to the rectifier. An additional column may also be required to remove water and ethanol from the impurities stream obtained as an overhead fraction from the hydroselective distillation, prior to disposing of the impurities e.g. by burning in a thermal oxidiser. The number of separate distillation columns required to achieve these functions in the accepted contemporary processes represents not only an enormous capital investment in terms of the plant but also decreases the economic efficiency of the process in terms of energy inputs, maintenance costs and incomplete recovery of products. Some expedients have been suggested to reduce the actual number of columns but these expedients have involved fewer columns which are nevertheless much larger to make up for the volume and capacity of the columns omitted. Consequently there is no appreciable saving either in capital costs or energy inputs. It has now been found that by operating the distillations under specific conditions the process can be reduced to no more than two columns, with actual reduction in total column capacity, energy inputs, maintenance and capital costs.

Accordingly, the present invention is a process for purifying crude ethanol to obtain substantially pure ethanol-water azeotrope, comprising separately feeding the crude ethanol and water into a single hydroselection column having a refluxing section above the water feed point, an intermediate section between the water feed point and the crude ethanol feed point, a stripping section between the crude ethanol feed point and a product side draw tray below the crude ethanol feedpoint, and a base section below the product side draw tray wherein the ratio of theoretical trays in the refluxing, intermediate and stripping sections is in the range 0.2–0.7:1:2-.0–2.5 the hydroselection column containing less than 100 actual trays and being operated at temperatures between 120° C. and 180° C. and at a pressure above 50 psia, the water being fed to the column at a point above the crude ethanol feed point and the molar ratio of water fed to ethanol in the crude ethanol feed being at least 10:1, withdrawing an overhead vapour fraction containing a substantial portion of the volatile impurities, and returning part of the overhead vapour fraction after condensation to the column as liquid reflux maintaining a reflux ratio of less than 200:1 expressed on the total amount of fluid removed from the column above the water feed point, withdrawing a purified aqueous ethanol sidestream substantially free from all impurities from the product side draw tray below the crude ethanol feed point, feeding the purified aqueous ethanol into the lower half and optionally aqueous alkali into the upper half of a rectification column, said column being operated at temperatures between 70° and 125° C. recycling an overhead purge stream containing acetaldehyde and other impurities from the rectification column to the crude ethanol feed to the hydroselection column, and withdrawing a substantially pure ethanol-water azeotrope containing less than 5 ppm of any of the impurities, except methanol, in the crude ethanol feed as a sidestream from the upper half of the column and an (alkaline) aqueous effluent substantially free from ethanol from the base of the column.

The crude ethanol fed to the hydroselection column suitably contains between 5 and 20% by weight of ethanol, preferably between 10 and 15% by weight of ethanol. The molar ratio of water fed to the ethanol in the crude ethanol feed is at least 10:1, and preferably from 11 to 13:1. The feeds to the hydroselection column are suitably fed at or below their respective bubble points at the appropriate feed tray pressure. The hydroselection column suitably has at least 66 actual trays and preferably between 70 and 90 actual trays.

The temperature profile within the hydroselection column is chosen to maximise the relative difference in volatilities between impurities and ethanol. It is preferably between 125° and 160° C. The pressure in the hydroselection column is suitably between 70 and 100 psia, preferably between 75 and 90 psia.

Operating under these conditions, an overhead vapour fraction containing substantially all of the volatile impurities is withdrawn from the column. The bulk of these overhead vapours are refluxed after condensation and returned to the top tray of the column suitably maintaining a reflux ratio of less than 100:1, preferably in the range of 40 to 60:1 expressed on the total amount of fluid removed from the column above the water feed point. The reason for using this as the basis of the reflux ratio is to take into consideration the fluids removed as a distillate product or as a purge stream (the butanols stream) above the water feed point. It will be clear to those skilled in the art that reflux ratios may be varied enormously if only one of the two e.g. distillate product, is used as the basis for calculation. In this reflux system the liquid reflux is normally a single phase liquid, but if two phases are present these should be adequately mixed before being returned as reflux to the top of the column. The remainder of the overhead vapour fraction containing the bulk of the volatile impurities contained in the feed is disposed of e.g. by feeding to a conventional thermal oxidiser. In addition to the distillate product removed, it is possible to remove a sidestream as purge above the water feed point. For example, under the conditions of the present invention if a purge stream is removed between the second and eighth tray from the head of the column and above the water feed point, such as stream will consist largely of the butanols and the removal of this stream will enable the other impurities to be further concentrated in the section above the purge before being taken off overhead. The removal of such a purge stream will therefore allow more impurities to be removed from the column with less ethanol losses overhead.

The purified aqueous ethanol withdrawn as a sidestream from the hydroselection column below the water feed point is substantially free from all impurities, particularly the butanols, which thus eliminates the need for a further column for the removal of butanols. The sidestream containing the purified aqueous ethanol is fed into the lower half of the rectification column, and optionally aqueous alkali is fed into the top half of this column. Aqueous alkali may not be necessary for purifying certain varieties of fermentation ethanol which do not produce acetaldehyde as an impurity. The feed rate of the aqueous alkali, where used, may be for example in the range 5 to 8 liters, preferably 5 to 6 liters, of 20% w/w aqueous caustic soda per 1000 liters of ethanol azeotrope product. The rectification column perferably has between 65 and 75 trays. This column is preferably operated at a temperature between 75° C. and 120° C. The head pressure in this column may vary, and may be for instance sub-atmospheric, atomspheric, or superatmospheric e.g. up to 25 psia or higher. Under these conditions the rectifier is confined to separating ethanol from the bulk of the water and a substantially pure azeotrope stream containing between 85 and 89 mole % of ethanol is recovered as a sidestream from a point above the aqueous alkali feed, if any, to the column. This ethanol-water azeotrope contains less than 5 ppm of any of the impurities, except methanol, in the starting material and under optimum conditions it is possible to reduce this level below 1 ppm of each impurity. The exception with regard to methanol impurity only arises in the case where the crude ethanol is produced by a fermentation process. Reflux to the rectification column is provided in the usual way by recycling condensed overhead vapours. A small overhead purge stream from this column is recycled back to the hydroselection column by mixing it with the crude ethanol feed to that column. Optionally, a small sidestream from the lower half of the rectification column may also be recycled to the crude ethanol feed to the hydroselection column further to improve the quality of the ethanol-water azeotrope product. Another feature of the present invention is that the alkaline aqueous effluent removed from the base of the rectification column is substantially free from ethanol.

The above procedure of obtaining substantially pure ethanol-water azeotrope may be used for crude ethanol whether produced by the synthetic or the fermentation route.

The invention is further illustrated in the accompanying flow diagram.

In the process shown in the accompanying FIGURE the crude ethanol is fed directly into the top half of the hydroselection column 4 via line 11. In the hydroselection column 4 the ratio of theoretical trays in the refluxing, intermediate and stripping sections is in the range 0.2–0.7:1:2.0–2.5 and the column contains at least 66 actual trays. Water is also fed into column 4 via line 12. The molar ratio of water fed via line 12 to the ethanol content of the feed via line 11 is at least 10:1. By operating at these dilutions the volatilities of the major impurities are inverted relative to ethanol and substantially all the butanols, a major portion of the aldehydes and diethyl ether are removed as overheads via line 15. Column 4 is operated with a liquid reflux via line 16 which is formed by feeding the overheads via line 15 into a condenser and reboiler cum condenser 5 and an impurities purge stream containing butanols, ethers and aldehydes is withdrawn via line 17 for the purpose of burning in the thermal oxidiser 9. An aqueous stream 13 is withdrawn from the base of column 4, a part of which is recycled after cooling via line 12 as the water feed to the column. The remainder maybe disposed of as effluent. A purified aqueous ethanol side stream substantially free from butanols is withdrawn from column 4 via line 14 and fed to the lower half of a rectification column 6. Caustic alkali is also fed to column 6 via line 18. An overhead purge stream containing acetaldehyde and other impurities is withdrawn from this column via line 20 part of this stream being returned as reflux via line 21 through a condenser 7, the remainder being returned to the crude ethanol feed line 11 via line 1. A purge side stream is removed from column 4 at a point above the water feed point. Such stream consists largely of butanols. Substantially pure ethanol-water azeotrope containing only a marginal excess of water and less than 5 ppm of impurities is withdrawn via line 19 for storage and/or drying at 8. This can be dried as and when necessary by known methods. A bottoms fraction consisting of alkaline water containing substantially no ethanol is withdrawn from the base of column 6 via line 3 and discharged as effluent. If necessary a purge stream can be withdrawn from column 6 via line 2 and recycled to the crude ethanol feed line 11.

It will be understood by those skilled in the art that the references to trays in the various columns are meant to include equivalent heights of column packing to achieve a similar split of the products.

The invention is further illustrated with reference to the following Example.

EXAMPLE

A stream of crude synthetic aqueous ethanol (containing by weight 12.96% ethanol, 0.158% diethylether, 0.022% secondary and tertiary butanols, and 0.035% acetaldehyde) produced by catalytic hydration of ethylene was fed as a liquid into an 80-tray hydroselection column on the 58th tray. A calculated amount of water was also fed into the hydroselection column on the 76th tray to maintain a molar ratio of water fed to the ethanol content in the feed to the column at about 11.3:1. The hydroselection column was operated with a temperature profile of between 122° C. (at the top) and 159° C. (at the base) and a head pressure of 88 psia, with a reflux above the water feed point. From the column an overhead vapour fraction containing substantially all of the volatile impurities was withdrawn and part of this fraction was condensed and returned to the column as reflux to maintain a reflux ratio of 50:1 expressed on the distillate product. The rest of the fraction was fed into a thermal oxidiser to be burnt. A purified aqueous ethanol stream (containing as impurities less than 1 ppm secondary butanol, less than 1 ppm tertiary butanol, less than 1 ppm acetaldehyde and less than 1 ppm diethyl ether) was withdrawn as vapour from the column between product side draw trays 18 and 19. The base product from this column was mainly water which could be discarded as effluent or optionally recycled to the water feed to the column. The purified aqueous ethanol withdrawn from the product side draw tray was fed into a 70 tray rectifying column on the 16th tray. An aqueous solution of caustic alkali (concentration 20% by weight) was introduced into the column on the 51st tray. This column was operated with a temperature profile of between 78° C. (at the top) and 112° C. (at the base), and a head pressure of 15 psia. A small overhead purge stream containing acetaldehyde and other impurities was recycled to the aqueous ethanol feed to the hydroselection column. A substantially pure ethanol-water azeotrope (containing between 86 and 87% molar of ethanol and less than 1 ppm of each of the impurities) was withdrawn as a side stream from the 63rd tray of this column. The base product from this column was an aqueous alkaline effluent which contained only traces of ethanol (2 ppm).

The surprising feature of this invention is that although the reflux ratio in the hydroselection column is only 50:1, which implies that a large fraction of the distillate product is withdrawn, yet the amount of ethanol in the distillate product removed is no greater than the case where the reflux ratio is above e.g. 200:1. Moreover, in spite of the elimination of the ether flash column, the amount of diethyl ether in the eventual azeotrope is less than 1 ppm. Thus the lower reflux ratios used and the elimination of the ether flash column result in substantially lower energy inputs into the hydroselection column.

We claim:

1. A process for purifying crude ethanol to obtain substantially pure ethanol-water azeotrope, comprising separately feeding the crude ethanol and water into a single hydroselection column having a refluxing section above the water feed point, an intermediate section between the water feed point and the crude ethanol feed point, a stripping section between the crude ethanol feed point and a produce side draw tray below the crude ethanol feed point, and a base section below the prouduct side draw tray wherein the ratio of theoretical trays in the refluxing, intermediate and stripping sections is in the range 0.2–0.7:1:2.0–2.5, the hydroselection column containing less than 100 actual trays and being operated at temperatures between 120° C. and 180° C. and at a pressure above 50 psia, the water being fed to the column at a point above the crude ethanol feed point and the molar ratio of water fed to ethanol in the crude ethanol feed being at least 10:1, withdrawing an overhead vapour fraction containing a substantial portion of volatile impurities, and returning part of the overhead vapour fraction after condensation to the column as liquid reflux maintaining a reflux ratio of less than 100:1 expressed on the total amount of fluid removed from the column above the water feed point, withdrawing a purified aqueous ethanol sidestream substantially free of all impurities from the produce side draw tray below the crude ethanol feed point, feeding the purified aqueous ethanol into the lower half of a rectification column, said column being operated at temperatures between 70° and 125° C. recycling an overhead purge stream containing acetaldehyde and other impurities from the rectification column to the crude ethanol feed to the hydroselection column, withdrawing a purge stream from the head of the hydroselection column at a point above the water feed point, and withdrawing a substantially pure ethanol-water azeotrope containing less than 5 ppm of any of the impurities, except methanol, in the crude ethanol feed as a side-stream from the upper half of the column and an aqueous effluent substantially free from ethanol from the base of the column.

2. A process according to claim 1 wherein said crude ethanol is synthetic ethanol and aqueous alkali is fed into the upper half of said rectification column.

3. A process according to claim 1 or claim 2 wherein the overheads returned to the hydroselection column as liquid reflux is maintained at a reflux ratio of between 40:1 and 60:1 expressed on the total amount of fluid removed from the column above the water feed point.

4. A process according to claim 1 or claim 2 wherein the crude ethanol fed to the hydroselection column contains between 5 and 20% by weight of ethanol.

5. A process according to claim 1 or 2 wherein the molar ratio of water fed to the ethanol in the crude ethanol feed is from 11 to 13:1.

6. A process according to claim 1 or 2 wherein the feeds to the hydroselection column are fed at or below their respective bubble points at the appropriate feed tray pressure.

7. A process according to claim 1 or 2 wherein the hydroselection column has between 70 and 90 actual trays.

8. A process according to claim 1 or 2 wherein the head pressure in the hydroselection column is between 70 and 100 psia.

9. A process according to claim 1 or 2 wherein the hydroselection column is operated at a temperature of between 125° and 160° C.

10. A process according to claim 1 or 2 wherein the rectification column is operated at a temperature between 75° C. and 120° C. and a pressure between atmospheric and 25 psia.

* * * * *

UNITED STATES PATENT AND TRADEMARK OFFICE
CERTIFICATE OF CORRECTION

PATENT NO.   :   4,448,644

DATED        :   May 15, 1984

INVENTOR(S)  :   BRIAN R. FOSTER and WILLIAM T. WOODFIN

It is certified that error appears in the above-identified patent and that said Letters Patent is hereby corrected as shown below:

Col. 3, line 22, "as" should read --a--

Col. 3, line 43, "perferably" should read --preferably--

In the Claims: Col 5

Claim 1, line 59, "prouduct" should read --product--

Signed and Sealed this

Twelfth Day of March 1985

[SEAL]

Attest:

DONALD J. QUIGG

Attesting Officer        Acting Commissioner of Patents and Trademarks